US009889261B2

(12) United States Patent
Arimoto et al.

(10) Patent No.: US 9,889,261 B2
(45) Date of Patent: Feb. 13, 2018

(54) NEBULIZER MESH AND PRODUCTION METHOD THEREOF

(71) Applicant: Tanaka Kikinzoku Kogyo K.K., Chiyoda-Ku (JP)

(72) Inventors: Tasuku Arimoto, Hiratsuka (JP); Makoto Sakai, Hiratsuka (JP); Yoshio Shindo, Hiratsuka (JP); Yuji Uchiumi, Hiratsuka (JP); Shingo Watanabe, Hiratsuka (JP)

(73) Assignee: Tanaka Kikinzoku Kogyo K.K., Tokyo (JP)

( * ) Notice: Subject to any disclaimer, the term of this patent is extended or adjusted under 35 U.S.C. 154(b) by 19 days.

(21) Appl. No.: 15/212,047

(22) Filed: Jul. 15, 2016

(65) Prior Publication Data

US 2016/0375203 A1 Dec. 29, 2016

Related U.S. Application Data

(62) Division of application No. 14/763,231, filed as application No. PCT/JP2014/051270 on Jan. 22, 2014, now Pat. No. 9,700,685.

(30) Foreign Application Priority Data

Jan. 24, 2013 (JP) .................................. 2013-011130

(51) Int. Cl.
*B05B 1/14* (2006.01)
*A61M 11/00* (2006.01)
(Continued)

(52) U.S. Cl.
CPC ...... *A61M 11/003* (2014.02); *A61M 15/0085* (2013.01); *B05B 1/26* (2013.01);
(Continued)

(58) Field of Classification Search
CPC ............. A61M 11/03; A61M 15/0085; A61M 2205/0244; A61M 2207/00;
(Continued)

(56) References Cited

U.S. PATENT DOCUMENTS 5,435,282 A * 7/1995 Haber ............... A61M 15/0065
128/200.14
6,530,370 B1 * 3/2003 Heinonen ............ A61M 11/005
128/200.14
(Continued)

FOREIGN PATENT DOCUMENTS

JP 64-062491 A 3/1989
JP H04-100557 A 4/1992
(Continued)

OTHER PUBLICATIONS

PCT, International Search Report PCT/JP2014/051270, dated Feb. 25, 2014.
(Continued)

*Primary Examiner* — Davis Hwu
(74) *Attorney, Agent, or Firm* — Orrick, Herrington & Sutcliffe LLP; Joseph A. Calvaruso

(57) ABSTRACT

The present invention relates to a nebulizer mesh which is used, in a nebulizer for atomizing and nebulizing liquid, for atomizing the liquid, and has plural through holes 17, wherein each of the through holes 17 forms a cylindrical space portion 174 on one surface side of the nebulizer mesh, and forms an opening 172 opened in a mortar shape on the other surface side, and to a production method thereof.

9 Claims, 9 Drawing Sheets

(51) Int. Cl.
  *A61M 15/00* (2006.01)
  *B05B 1/26* (2006.01)
  *C25D 3/50* (2006.01)
  *C25D 5/02* (2006.01)
  *C25D 5/48* (2006.01)
  *C25D 5/54* (2006.01)
  *C25D 7/04* (2006.01)
  *B05B 17/00* (2006.01)
  *C25D 1/08* (2006.01)

(52) U.S. Cl.
  CPC ............ *B05B 17/0646* (2013.01); *C25D 1/08* (2013.01); *C25D 3/50* (2013.01); *C25D 5/02* (2013.01); *C25D 5/022* (2013.01); *C25D 5/48* (2013.01); *C25D 5/54* (2013.01); *C25D 7/04* (2013.01); *A61M 2205/0244* (2013.01); *A61M 2207/00* (2013.01)

(58) Field of Classification Search
  CPC ... A61M 11/005; A61M 15/0065; C25D 3/50; C25D 5/02; C25D 5/48; C25D 5/54; C25D 7/04; C25D 1/08; C25D 5/022; B05B 1/26; B05B 17/0646
  USPC .............................................. 239/590.3, 338
  See application file for complete search history.

(56) References Cited

U.S. PATENT DOCUMENTS

| | | | | |
|---|---|---|---|---|
| 6,550,472 B2* | 4/2003 | Litherland | ........... | A61M 11/005 128/200.14 |
| 8,382,008 B1* | 2/2013 | Ricciardi | ................. | A61L 2/22 128/200.16 |
| 2002/0121274 A1 | 9/2002 | Borland et al. | | |
| 2004/0256487 A1* | 12/2004 | Collins, Jr. | .......... | A61M 11/005 239/338 |
| 2009/0242661 A1 | 10/2009 | Lu | | |

FOREIGN PATENT DOCUMENTS

| | | |
|---|---|---|
| JP | H09-217191 A | 8/1997 |
| JP | H09-323054 A | 12/1997 |
| JP | 2001-149834 A | 6/2001 |
| JP | 2002-59552 A | 2/2002 |
| JP | 2003-1829 A | 1/2003 |
| JP | 2006-297226 A | 11/2006 |
| JP | 2011-235202 A | 11/2011 |

OTHER PUBLICATIONS

JP, Office Action—JP 2013-011130—Notification of Reason for Refusal, dated Jun. 24, 2014.
JP, Office Action—JP 2013-011130—Decision of Refusal, dated Oct. 28, 2014.
JP, Office Action—JP 2013-011130—Notification of Release of Pretrial Reexamination, dated May 27, 2015.
JP, JP 2013-011130—Explanation of Circumstances Concerning Accelerated Examination, dated May 21, 2014.
JP, JP 2013-011130—Demand for Trial, Jan. 28, 2015.
JP, Office Action—JP 2013-011130—Notification of Reason for Refusal, dated Mar. 8, 2016.
JP, JP 2013-011130—Amendment, dated Mar. 11, 2015.
Decision of Refusal dated May 9, 2017 in the corresponding Japanese patent application No. 2015-014659 and English translation thereof.
Extended European Search Report dated Sep. 2, 2016 in the corresponding European patent application No. 14743039.1.
JP-appeal dated Aug. 9, 2017 in the corresponding Japanese patent application No. 2015-014659 and English translation thereof.

* cited by examiner

NEBULIZER MESH AND PRODUCTION METHOD THEREOF

RELATED APPLICATIONS

This application is a divisional of co-pending application Ser. No. 14/763,231 filed Jan. 22, 2014, which is based on Japanese Patent Application No. 2013-011130 filed on Jan. 24, 2013, which the disclosures of both applications are incorporated by reference herein in their entirety and for all purposes.

TECHNICAL FIELD

The present invention relates to a nebulizer mesh which is used in treatment of respiratory system diseases and the like, and to a production method thereof. More particularly, the present invention relates to a nebulizer mesh which is used for atomizing a liquid and controlling the particle diameter and has plural through holes in a nebulizer for atomizing and nebulizing the liquid, and to a production method thereof.

BACKGROUND ART

In order to enhance the effects of treatment, nebulizers which are used in treatment of respiratory system diseases are required to have performance to allow a drug solution to efficiently reach a target affected area. When the particle diameter of a drug solution to be nebulized is decreased, it becomes possible for particles of the drug solution to reach the bronchi, the bronchioles located back thereof, and further the alveoli. In addition, the effects of treatment can be enhanced by ensuring a sufficient nebulized amount. Accordingly, in order to improve the performance of the nebulizer, it is necessary to decrease the particle diameter of the drug solution to be nebulized from the nebulizer and to increase the nebulized amount.

An electroforming method has conventionally been used for hole processing of a nebulizer mesh (for example, see Patent Documents 1 and 2). The hole processing of the nebulizer mesh using the conventional electroforming method is described based on FIGS. 5(a) to 5(e).

FIG. 5 shows cross-sectional views for illustrating steps of obtaining the nebulizer mesh by applying thick electroplating onto a Cu substrate as a matrix. First, as shown in FIG. 5(a), a matrix 51 is prepared. The matrix 51 includes, for example, a Cu substrate. Then, as shown in FIG. 5(b), a resist pattern 52 is formed in a predetermined shape on the matrix 51. The shape thereof is, for example, circular.

Subsequently, as shown in FIG. 5(c), for example, thick electroplating using platinum as a main component is performed to deposit an electroformed film 53. The electroformed film 53 is initially deposited on a portion of the matrix 51 which is not covered with the resist pattern 52, and grows only in a direction perpendicular to a plane of the matrix 51 (in a longitudinal direction). However, when the thickness of the electroformed film 53 reaches the thickness of the resist pattern 52 or more, the electroformed film 53 grows also in a direction parallel to the plane of the matrix 51 (in a lateral direction).

Thereafter, when the thick electroplating is stopped before the resist pattern 52 is completely covered with the electroformed film 53, the electroformed film 53 as shown in FIG. 5(c) is obtained. Then, as shown in FIGS. 5(d) and 5(e), the matrix 51 and the resist pattern 52 are separated to obtain the nebulizer mesh.

CITATION LIST

Patent Documents

Patent Document 1: JP-A-9-323054
Patent Document 2: JP-A-9-217191

SUMMARY OF THE INVENTION

Problems to be Solved by the Invention

However, according to the conventional electroforming methods, it is difficult to properly control the size of through holes, which has caused problems of variation in the nebulized amount among products and poor production yields.

It is therefore an object of the present invention to provide a nebulizer mesh having plural through holes from which a liquid is atomized and nebulized, in which the diameter of droplet particles to be nebulized can be sufficiently decreased by properly controlling the size of the through holes, and the production yields are enhanced by suppressing variation in the nebulized amount among products; and a production method thereof.

Means for Solving the Problems

As a result of intensive studies, the present inventors have found that the above-mentioned problems can be solved by employing particular steps using two resist patterns and forming through holes formed in a nebulizer mesh into a specific shape, thus completing the present invention.

That is to say, the present invention is as follows:

1. A nebulizer mesh which is used, in a nebulizer for atomizing and nebulizing liquid, for atomizing the liquid, and has plural through holes, wherein each of the through holes forms a cylindrical space portion on one surface side of the nebulizer mesh, and forms an opening opened in a mortar shape on the other surface side.

2. The nebulizer mesh described in 1 above, which is composed of platinum as a main component.

3. The nebulizer mesh described in 1 or 2 above, wherein the cylindrical space portion has a height of from 0.1 μm to 20 μm.

4. The nebulizer mesh described in any one of 1 to 3 above, wherein the cylindrical space portion has a diameter of from 0.3 μm to 10 μm.

5. The nebulizer mesh described in any one of 1 to 4 above, wherein particles nebulized from the nebulizer mesh has an average particle diameter of from 1 μm to 15 μm.

6. A method for producing a nebulizer mesh which is used, in a nebulizer for atomizing and nebulizing liquid, for atomizing the liquid, and has plural through holes, comprising: a first step of forming a first resist pattern in a predetermined shape on a matrix; a second step of subsequently forming a second resist pattern in a cylindrical shape on the first resist pattern; a third step of performing metal plating and forming through holes of the nebulizer mesh, after the second step; and a fourth step of removing the matrix and the first and second resist patterns, wherein each of the through holes formed by the third step forms a cylindrical space portion on one surface side of the nebulizer mesh and forms an opening opened in a mortar shape on the other surface side, and the shape of the cylindrical space portion of the through hole is determined by the shape of the second resist pattern formed in the second step.

7. The method for producing a nebulizer mesh described in 6 above, wherein the nebulizer mesh is composed of platinum as a main component.

8. The method for producing a nebulizer mesh described in 6 or 7 above, wherein the cylindrical space portion has a height of from 0.1 μm to 20 μm.

9. The method for producing a nebulizer mesh described in any one of 6 to 8 above, wherein the cylindrical space portion has a diameter of from 0.3 μm to 10 μm.

10. The method for producing a nebulizer mesh described in any one of 6 to 9 above, wherein a resist for forming the first resist pattern is a polyimide-based resist, and a resist for forming the second resist pattern is an epoxy-based resist.

Effect of the Invention

According to a nebulizer mesh of the present invention and a production method thereof, particular steps using two resist patterns are employed, and through holes formed in the nebulizer mesh is formed into a specific shape, so that there can be achieved effects of being able to sufficiently decrease the diameter of droplet particles to be nebulized by properly controlling the size of the through holes and being able to enhance the production yields by suppressing variation in the nebulized amount among products.

EMBODIMENTS FOR CARRYING OUT THE INVENTION

Modes for carrying out the present invention are described below in more details.

Figure 1:
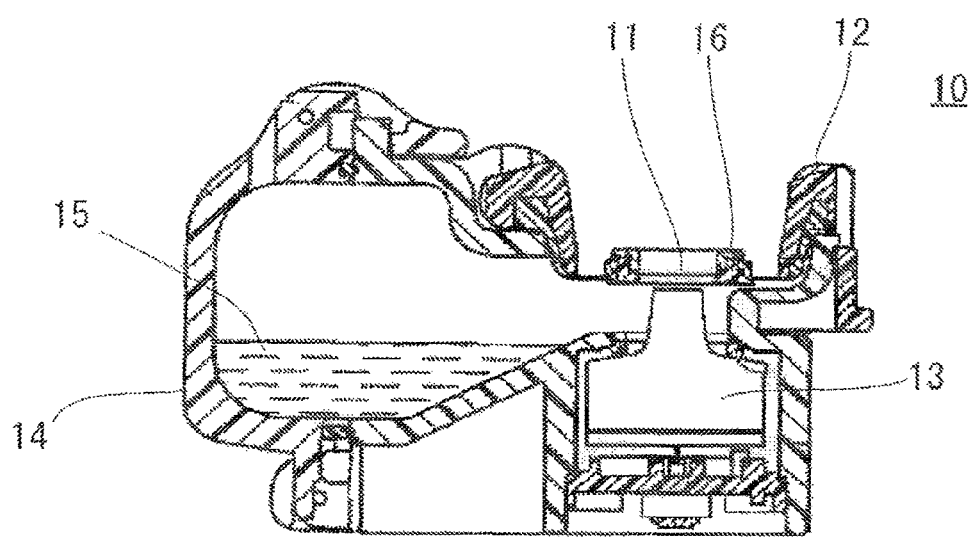
FIG. 1 is a schematic cross-sectional view showing a constitution in the case where a nebulizer mesh of the present invention is used in an atomizing inhalator (nebulizer) of the ultrasonic vibration type.
Figure 2:
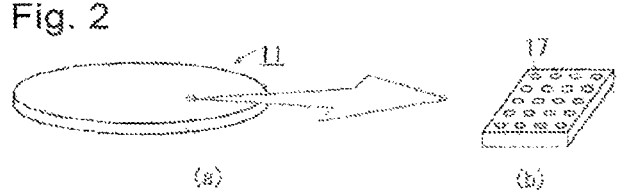
FIG. 2(a) is a perspective view showing the appearance of a mesh.
FIG. 2(b) is a partially enlarged view thereof.

A constitution of a nebulizer for carrying out the present invention is shown in FIG. 1, but the invention should not be construed as being limited to the constitution in any way. FIG. 1 is a schematic cross-sectional view showing a constitution in the case where a nebulizer mesh of the present invention (hereinafter also simply referred to as a mesh) is used in a nebulizing inhalator (nebulizer) 10 of the ultrasonic vibration type. The inhalator 10 has such a structure that a mesh 11 having plural fine through holes, as shown in FIG. 2, is fixed to an inside of a casing 12; that a top surface of a vibrator 13 is pressed against a bottom surface of the mesh 11; and that an end portion of the vibrator 13 is contactable with a liquid 15 stored in a thank 14. Further, the mesh 11 is held by a mesh support 16.

The mesh 11 used in the inhalator 10 is constituted by a large number of sufficiently fine through holes 17, as shown in FIG. 2, in order to finely granulate (atomize) the liquid 15. FIG. 2 is a perspective view (a) and a partially enlarged view (b) showing the appearance of the mesh 11. As shown in FIG. 2(a), the mesh 11 has a plate-like outer shape. In addition, as shown in FIG. 2(b), the mesh 11 has the plural through holes 17.

When the vibrator 13 is vibrated up and down, the mesh 11 pressed to the vibrator 13 with appropriate force by the mesh support 16 resonates due to microvibration of the vibrator 13. When the mesh 11 resonates, negative pressure is generated between the mesh 11 and the vibrator 13. Accordingly, the liquid 15 in the tank 14 is sucked up to a top surface of the vibrator 13. The liquid 15 thus sucked up between the mesh 11 and the vibrator 13 passes through the fine through holes 17 due to vibration of the mesh 11, and the atomized liquid 15 is nebulized into the outside air.

Figure 3:
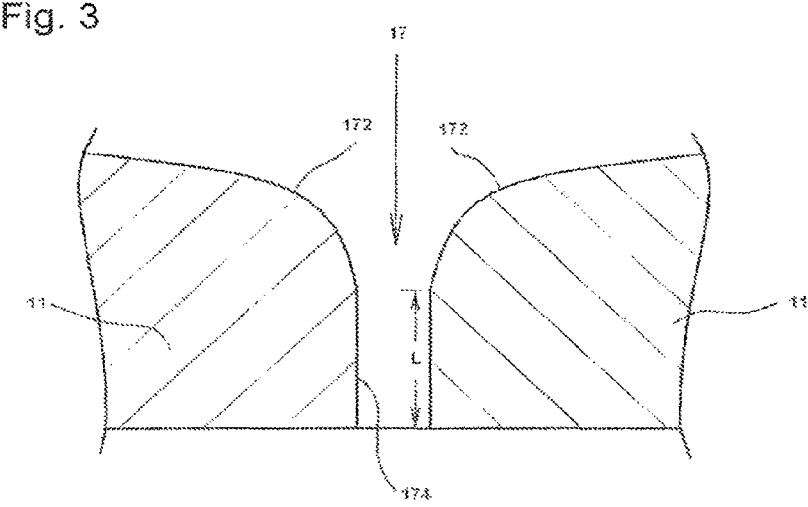
FIG. 3 is a cross-sectional view for illustrating a through hole of a mesh.
Figure 4A:
FIGS. 4(a) to 4(e) are cross-sectional views for illustrating steps for producing a mesh of the present invention.
Figure 4B:
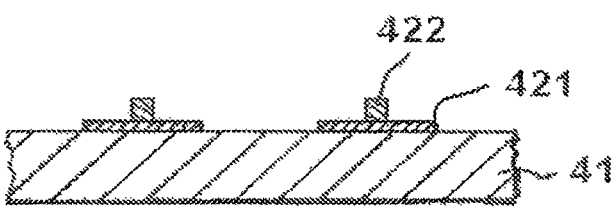
Figure 4C:
Figure 4D:
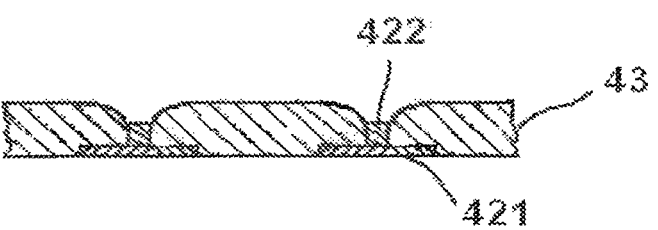
Figure 4E:
Figure 5A:
FIGS. 5(a) to 5(e) are cross-sectional views for illustrating steps for producing a nebulizer mesh by a conventional electroforming method.
Figure 5B:
Figure 5C:
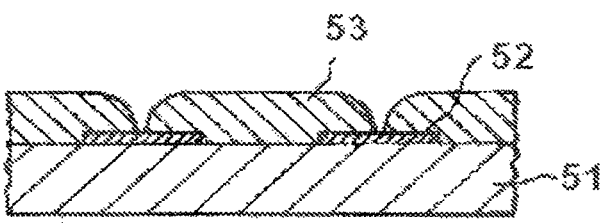
Figure 5D:
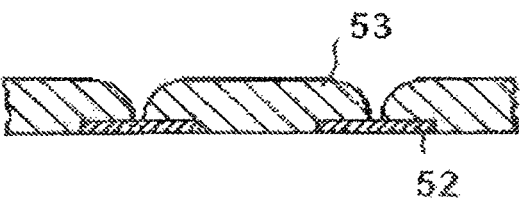
Figure 5E:

FIG. 3 is a cross-sectional view of a nebulizer mesh of the present invention for illustrating the through holes 17 of the mesh.

The through hole 17 forms a cylindrical space portion 174 on one surface side of the mesh 11, and forms an opening 172 opened in a mortar shape on the other surface side. That is to say, the above-mentioned other surface side of the through hole 17 forms the opening 172 of the other surface side with gradually increasing the hole diameter from the cylindrical space portion 174 of one surface side of the nebulizer mesh 11. In the present invention, this shape is called a "mortar shape."

It is considered that the volume of the liquid passing through the cylindrical portion becomes constant according to the above-mentioned shape, so that the particle diameter of the liquid also becomes constant due to surface tension, which has an effect of suppressing variation in the nebulized particle diameter caused by contact with a tone as an ultrasonic vibrating part. For this reason, when the liquid is delivered as a drug solution to an affected area or nebulized as a cosmetic liquid onto the skin surface, the liquid can be uniformly supplied. There can be achieved an effect of being able to control the particle diameter of the liquid atomized in high nebulized amounts so as to decrease the variation.

The diameter of the cylindrical space portion 174 is, for example, from 0.3 μm to 10 μm, and preferably from 2 μm to 4 μm. Further, the length L of the cylindrical space portion 174 is, for example, from 0.1 μm to 20 μm, preferably from 0.5 μm to 10 μm, and more preferably from 1 to 8 μm.

The thickness of the nebulizer mesh of the present invention is preferably 10 μm or more, more preferably 15 μm or more, and still more preferably 20 μm or more. Further, it is preferably 300 μm or less, more preferably 100 μm or less, and still more preferably 30 μm or less. Sufficient strength can be secured by adjusting the thickness of the nebulizer mesh to 10 μm or more. Further, for example, when platinum is used, the density of platinum is increased by adjusting the thickness of the nebulizer mesh to 100 μm or less. Accordingly, the inertia mass can be prevented from being increased, and followability to ultrasonic vibrations can be suppressed from being deteriorated.

The number of the through holes 17 in the nebulizer mesh of the present invention is not particularly limited, and can be appropriately set according to the type of the liquid 15, the purpose and the like. However, usually, it is preferably 100 or more, more preferably 1000 or more, and still more preferably 10000 or more.

The diameter of particles nebulized by the nebulizer mesh of the present invention is preferably from 3 to 6 μm, more preferably from 3.5 to 5.5 μm, and still more preferably from 4.0 to 5.0 μm. An effect due to the liquid, such as a treatment effect, can be more improved by adjusting the diameter of nebulized particles to 3 to 6 μm. For example, it can be adjusted to such an optimum particle diameter that a drug solution reaches target organs such as the alveoli.

The average particle diameter of particles nebulized from the nebulizer mesh is measured by the following method. A mesh nozzle prepared is mounted on a nebulizer equipped with a horn vibrator, and a physiological saline solution is supplied as the liquid to a region in which the vibrator and the mesh nozzle are contacted with each other to be atomized. The average particle diameter of particles to be nebulized is measured by a laser light diffraction method using a particle diameter measurement apparatus. Specifically, measurement can be performed by a method described in detail in Example.

The nebulizer mesh of the present invention is preferably composed of platinum as a main component. "Composed of platinum as a main component" indicates that the content of platinum contained in a material constituting the nebulizer mesh is 50% by mass or more. The content of platinum contained in the material constituting the nebulizer mesh is 50% by mass or more, preferably 70% by mass or more, and more preferably 90% by mass or more.

Other components other than platinum, which are contained in the material constituting the nebulizer mesh, include, for example, precious metals such as gold, silver, iridium, rhodium, ruthenium and palladium, and valve metals such as titanium, zirconium, hafnium, niobium, tantalum, zinc, tungsten and bismuth.

According to the above-mentioned preferred embodiment, the nebulizer mesh of the present invention is composed of, as a main component, platinum having a high specific gravity as compared with other metals. Platinum has a specific gravity of 21.45 g/cm3, and, for example, nickel and palladium which have hitherto been used as materials of the nebulizer mesh have specific gravities of 8.902 g/cm3 and 12.02 g/cm3, respectively. The kinetic energy K is represented by K=½×(mv)2 (in the formula, m is a mass and v is a velocity), and the larger mass causes the higher kinetic energy. For that reason, high kinetic energy can be obtained at the time of nebulizing the liquid by containing, as a main component, platinum having a high specific gravity as compared with other metals, and a liquid having a high viscosity and a liquid having a high specific gravity can be nebulized, which makes it possible to perform stable nebulization with a low influence of the type of liquid and to increase the nebulized amount.

Further, the nebulizer mesh of the present invention has high biosafety from the viewpoints of metal allergy and carcinogenicity, by containing platinum as a main component. In addition, stiffness is secured and it becomes possible to decrease the thickness of the nebulizer mesh, by containing platinum as a main component. The liquid resistance is reduced by decreasing the thickness of the mesh, resulting in easier nebulization, so that the nebulized amount can be improved.

Next, a method for producing a nebulizer mesh according to the present invention will be described. The production method is characterized in that it comprises a first step of forming a first resist pattern in a predetermined shape on a matrix, a second step of subsequently forming a second resist pattern in a cylindrical shape on the above-mentioned first resist pattern, a third step of performing metal plating and forming through holes of the above-mentioned nebulizer mesh, after the above-mentioned second step, and a fourth step of removing the above-mentioned matrix and the above-mentioned first and second resist patterns, wherein each of the through holes formed by the above-mentioned third step forms a cylindrical space portion on one surface side of the above-mentioned nebulizer mesh and forms an opening opened in a mortar shape on the other surface side, and the shape of the cylindrical space portion of the above-mentioned through hole is determined by the shape of the second resist pattern formed in the above-mentioned second step.

FIG. 4 shows cross-sectional views for illustrating steps for producing the mesh of the present invention.

First, as shown in FIG. 4(*a*), a matrix 41 is prepared. As the matrix 41, there can be used, for example, a Cu substrate, a Ni substrate, an Ag substrate, an alloy thereof or the like. More preferably, Cu or an alloy thereof is used.

Then, as shown in FIG. 4(*b*), a first resist pattern 421 is formed in a predetermined shape on the matrix 41 (the first step). The shape is, for example, circular, and the diameter thereof is, for example, from 20 μm to 40 μm. Further, the thickness is, for example, from 0.5 μm to 2 μm.

Subsequently, a second resist pattern 422 is formed in a cylindrical shape on the first resist pattern 421 (the second step). The size of the second resist pattern 422 determines the size of the cylindrical space portion of the through hole, and may be appropriately determined according to the desired size of the cylindrical space portion.

Further, the formation of the respective resist patterns may be appropriately determined according to the type of resist used. The respective resist patterns can be formed, for example, through respective steps of application of a resist liquid onto the matrix 41, drying, exposure and development. In addition, the resist may be either positive or negative.

Subsequently, as shown in FIG. 4(*c*), plating of a metal composed of platinum as a main component, for example, thick electroplating, for example, is performed to deposit an electroformed film 43 (the third step). The electroformed film 43 is initially deposited on a portion of the matrix 41 which is not covered with the first resist pattern 421, and grows only in a direction perpendicular to a plane of the matrix 41 (in a longitudinal direction). However, when the thickness of the electroformed film 43 reaches the thickness of the first resist pattern 421 or more, the electroformed film 43 grows also in a direction parallel to the plane of the matrix 41 (in a lateral direction). Thereafter, when the plating is stopped at the time of coming into contact with the second resist and not exceeding the height, the electroformed film 43 as shown in FIG. 4(*c*) is obtained.

Thereafter, when the matrix 41, the first resist pattern 421 and the second resist pattern 422 are removed (the fourth step) as shown in FIGS. 4(*d*) and 4(*e*), the nebulizer mesh of the present invention having the through holes 17 is obtained in each of which the cylindrical space portion 174 is formed on one surface side and the opening 172 opened in a mortar shape is formed on the other surface side, as shown in FIG. 3 described above.

Incidentally, the plating liquids containing platinum as a main component include, for example, an aqueous solution containing a platinum salt such as dinitrodiamine platinum, hexahydroxo platinum, hexaammine platinum hydroxide or hexachloroplatinate, which is a water-soluble platinum salt.

Further, the platinum salt concentration in the plating liquid is preferably adjusted to from 5 to 50 g/L, in order to obtain stable deposition. Furthermore, electrolytic conditions are preferably adjusted to a liquid temperature of from 50 to 100° C. and a current density of from 0.5 to 5 A/dm2. The pH of the plating liquid is preferably adjusted to from 8 to 14.

In addition, when the plating liquid containing platinum as a main component as described above is used, a resist for forming the first resist pattern 421 is preferably a polyimide-based resist in which a polyimide-based resin is used as a base material component, because of its excellent alkali resistance and good adhesion with the matrix 41, and the second resist pattern 422 is preferably an epoxy-based resist in which an epoxy-based resin is used as a base material component, because of its excellent heat resistance.

As these resists, commercially available ones can be used. For example, the polyimide-based resists include EPPR-A (trade name) manufactured by Tokyo Ohka Kogyo Co., Ltd., and the epoxy-based resists include KMPR (trade name) manufactured by Kayaku Microchem Co., Ltd., and the like.

Incidentally, between the above-mentioned respective steps in the production method of the present invention, there can be provided etching, cleaning, a bake step and the like, as needed.

The nebulizer mesh of the present invention can be used in a medical equipment such as an inhalator shown in FIG. 1, and may be used in a beauty instrument such as a facial care device.

In the present invention, the "liquid" to which the nebulizer mesh is applied means, for example, an organic substance, an inorganic substance and a solution thereof, and a slurry liquid material of an organic substance, an inorganic substance and a ceramic substance. Preferably, an aqueous solution of an organic substance and/or an inorganic substance is used as the liquid. The liquids include, for example, a drug solution, a cosmetic material and the like.

EXAMPLES

The present invention will be further described below with reference to Examples and Comparative Example. However, the present invention should not be construed as being limited to the respective Examples.

Example 1

First, a matrix 41 was prepared as shown in FIG. 4(*a*). A Cu substrate was used as the matrix 41.

Then, as shown in FIG. 4(*b*), plural first resist patterns 421 were formed in a circular shape on the matrix 41 (the first step). The diameter of the circular shape is 32 μm, and the thickness is 1 μm. As a resist, there was used EPPR-A (trade name) manufactured by Tokyo Ohka Kogyo Co., Ltd., a polyimide-based resist, in the first resist patterns 421.

A spin coat method was employed for application of the resist. The exposure amount was adjusted to from 50 to 100 mJ/cm2. An EPPR developer manufactured by Tokyo Ohka Kogyo Co., Ltd. was used as a developer.

Subsequently, a second resist pattern 422 was formed in a cylindrical shape on the first resist pattern 421 (the second step). The second resist pattern 422 is in a cylindrical shape whose size is 2.5 μm in diameter and 2 μm, 4 μm, 6 μm or 8 μm in height. As a resist for forming the second resist pattern 422, there was used KMPR (trade name) manufactured by Kayaku Microchem Co., Ltd., an epoxy-based resist. Application of the resist was performed by the spin coat method. The exposure amount was adjusted to from 50 to 100 mJ/cm2. A KMPR developer manufactured by Kayaku Microchem Co., Ltd. was used as a developer.

Figure 6A:
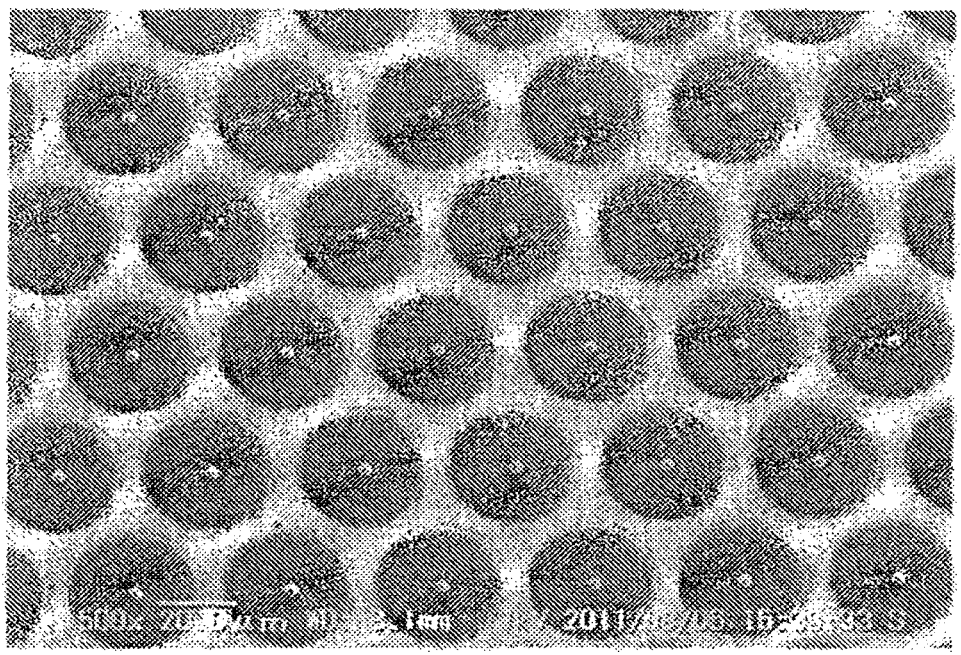
FIGS. 6(a) and 6(b) are electron micrographs from a top surface of a resist pattern formed in a second step in Example 1.
Figure 6B:
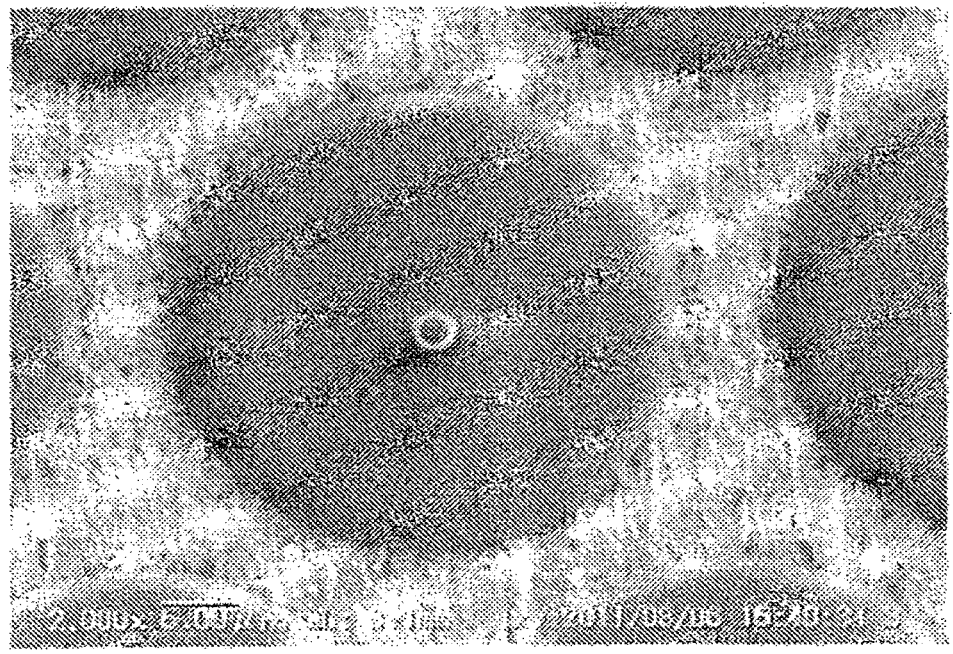

FIG. 6 shows electron micrographs from a top surface of the resist pattern formed in the second step. In FIG. 6, the size of the second resist pattern 422 is 2.5 μm in diameter and 8 μm in height. Further, FIG. 6(*a*) is at a magnification of 500×, and FIG. 6(*b*) is at a magnification of 2000×. As known from FIG. 6, it is found that the second resist pattern 422 is formed in a cylindrical shape on the first resist pattern 421 under a controlled state.

Then, as shown in FIG. 4(*c*), platinum was plated on the matrix 41 by thick electroplating, and an electroformed film 43 was deposited (the third step). The electroformed film 43 was initially deposited on a portion of the matrix 41 which was not covered with the first resist pattern 421, and grew only in a direction perpendicular to a plane of the matrix 41 (in a longitudinal direction). However, when the thickness of the electroformed film 43 reached the thickness of the first resist pattern 421 or more, the electroformed film 43 grew also in a direction parallel to the plane of the matrix 41 (in a lateral direction). Thereafter, when the thick electroplating was stopped before the resist pattern 422 was completely covered with the electroformed film 43, the electroformed film 43 as shown in FIG. 4(*c*) was obtained.

Electroplating conditions were set to the following conditions:

Current density: 2 A/dm2
Plating time: 70 minutes
Temperature: 90° C.

Figure 7A:
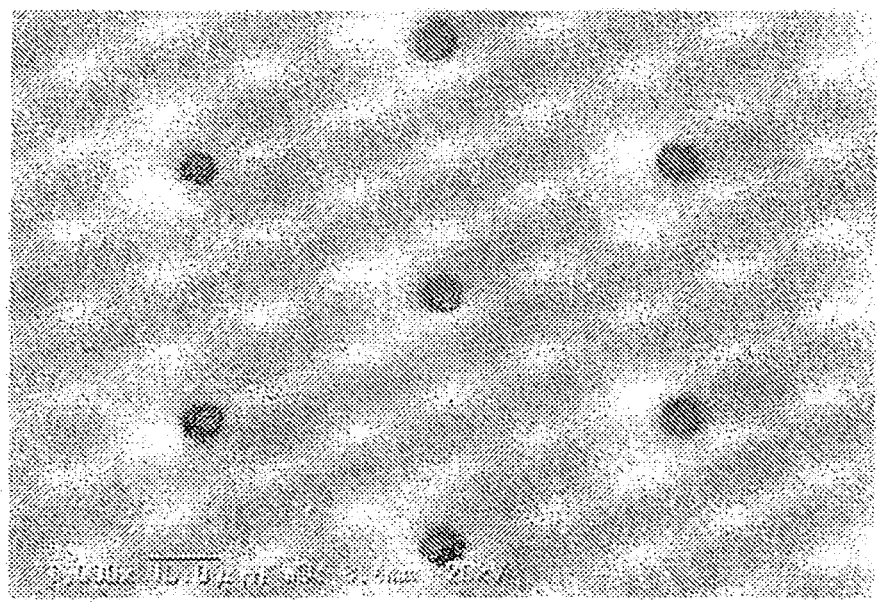
FIGS. 7(a) and 7(b) are electron micrographs from a top surface of an electroformed film 43 after plating in a third step in Example 1.
Figure 7B:
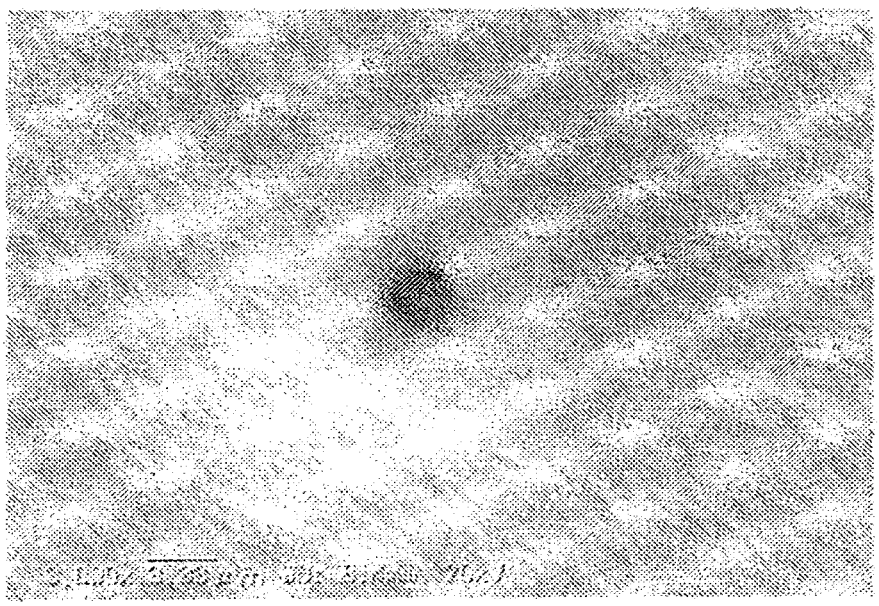

FIG. 7 shows electron micrographs from a top surface of the electroformed film 43 after the plating in the third step. FIG. 7(*a*) is at magnification of 1000×, and FIG. 7(*b*) is at a magnification of 3000×. As known from FIG. 7, it has been confirmed that the shape of through holes is not lost even after the plating, and that adhesion with the matrix 41 is also good.

Incidentally, a composition of a plating liquid used in Example 1 is as follows: PlaTinart (manufactured by Electroplating Engineers of Japan Ltd.), pH=13, Pt: 20 g/L Thereafter, the matrix 41, the first resist pattern 421 and the second resist pattern 422 were removed (the fourth step). As a removing liquid, there was used an EPPR removing liquid manufactured by Tokyo Ohka Kogyo Co., Ltd.

Figures 8A, 8B, 8C, 8D:
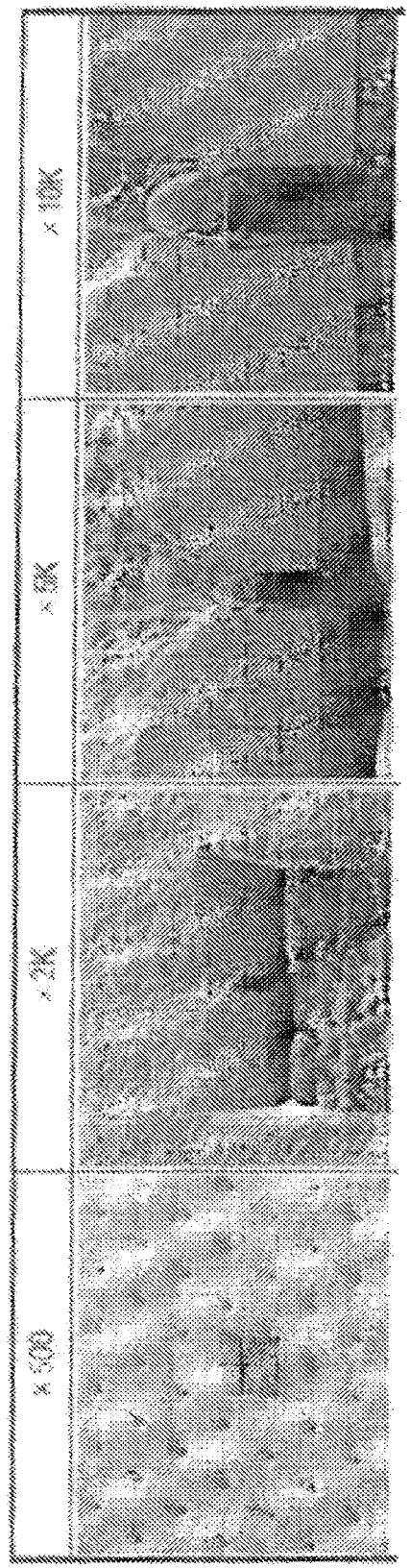
FIGS. 8(a) to 8(d) are cross-sectional photographs of a part of a through hole of a nebulizer mesh obtained in Example 1.

The cross-sectional shape of a part of the through hole obtained was observed under an electron microscope. FIG. 8 shows cross-sectional photographs of a part of the through hole of the nebulizer mesh obtained in Example 1. The magnification of FIG. 8 is 500× in 8(*a*), 2000× in 8(*b*), 5000× in 8(*c*) and 10000× in 8(*d*). As shown in FIG. 8, it has been known that the shape of the through hole has a cylindrical space portion on one surface side, and forms an opening opened in a mortar shape on the other surface side.

Further, it has been known that the diameter of the cylindrical space portion 174 is from 2.4 µm to 2.6 µm, and the length L of the cylindrical space portion 174 is from 7.8 µm to 8.2 µm.

The thickness of the nebulizer mesh was 20 µm.

Figure 9:
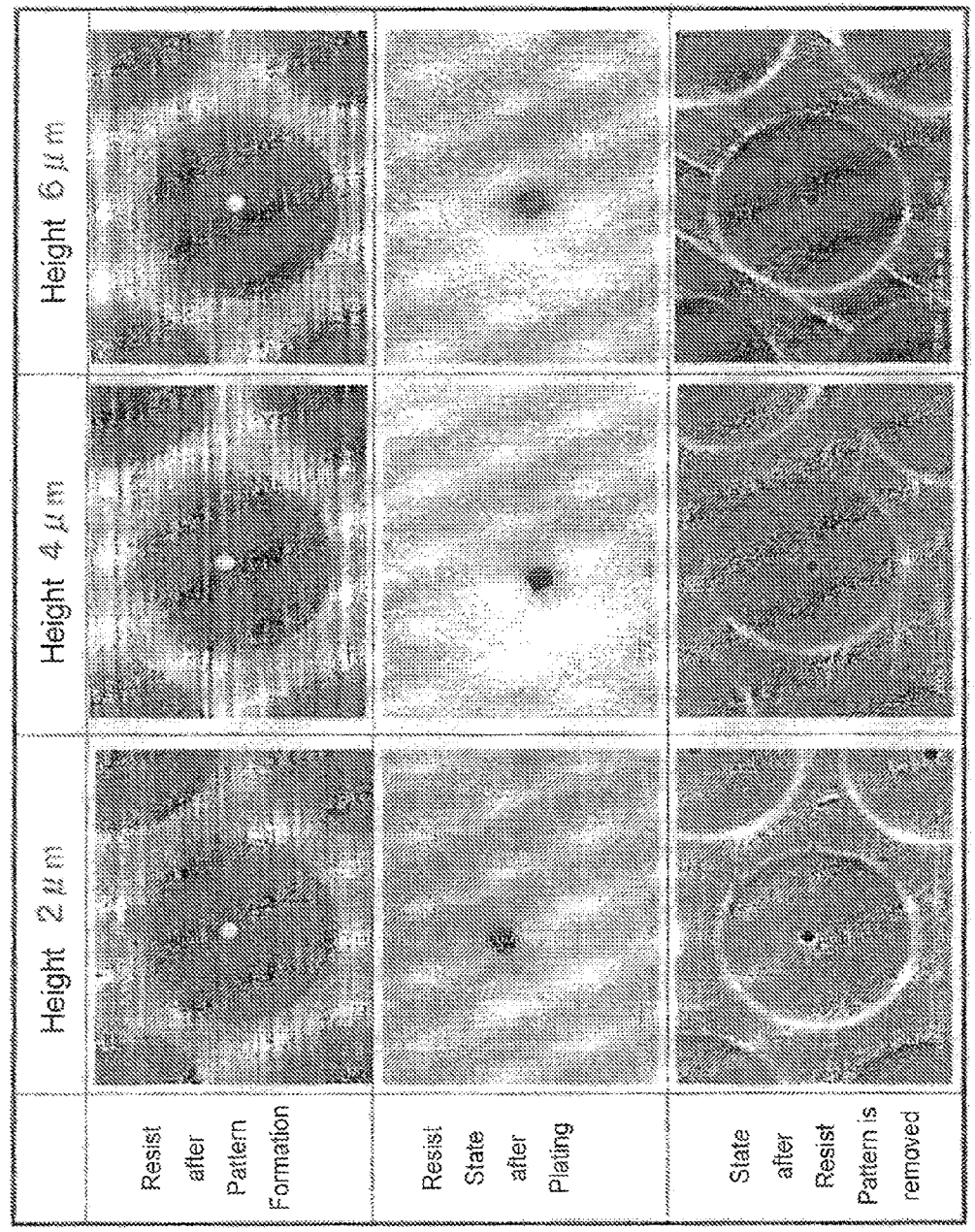
FIG. 9 shows electron microphotographs for illustrating a resist after resist pattern formation, a resist state viewed from the side of an electroformed film after plating and a state after a resist pattern on the reverse side thereof is removed, in the case where the height of a second resist pattern 422 is changed to 2 μm, 4 μm or 6 μm in Example 1.

FIG. 9 shows electron micrographs for illustrating the resist after pattern formation, a resist state seen from an electroformed film side after plating and a state after the resist pattern on the back side thereof has been removed, at the time when the height of the second resist pattern 422 is adjusted to 2 µm, 4 µm or 6 µm. From the results of FIG. 9, it has been known, even at any height, that the through hole has the cylindrical space portion on one surface side and forms the opening opened in a mortar shape on the other surface side without losing the shape thereof.

Example 2

A nebulizer mesh was prepared by the same resist application method and pattern formation method as in Example 1 except for using EPPR-A (trade name) manufactured by Tokyo Ohka Kogyo Co., Ltd. as both the first and second resists in the two-layer mesh. The first resist pattern 421 was adjusted to 32 µm in circular diameter and 1 µm in thickness. Further, the second resist pattern was adjusted to 2.5 µm in diameter and 3 µm in height.

Example 3

A nebulizer mesh was prepared by the same resist application method and pattern formation method as in Example 1 except for using KMPR (trade name) manufactured by Kayaku Microchem Co., Ltd. as both the first and second resists in the two-layer mesh. The first resist pattern 421 was adjusted to 32 µm in circular diameter and 1 µm in thickness. Further, the second resist pattern was adjusted to 2.5 µm in diameter and 3 µm in height.

With respect to Examples 2 and 3, the cross-sectional shape of a part of a through hole obtained was observed under an electron microscope. As a result, the shape of the through hole was not lost even after the plating, and the good shape was obtained. Incidentally, better adhesion with a copper plate as the matrix was obtained by using EPPR for the first resist.

Example 4

A nebulizer mesh was prepared by the same resist application method and pattern forming method as in Example 1. The first resist pattern 421 was adjusted to a circular diameter of 32 µm and a thickness of 1 µm. Further, the second resist pattern was adjusted to a height of 3 µm and three type of diameters of 1.5 µm, 2.0 µm and 2.5 µm. In all of the through holes obtained, the shape of the through holes was not lost even after the plating, and the good shape was obtained.

Comparative Example 1

A nebulizer mesh was prepared using a conventional electroforming method as shown in FIG. 5.

First, as shown in FIG. 5(*a*), a matrix 51 was prepared. A Cu substrate was used as the matrix 51.

Then, as shown in FIG. 5(*b*), plural first resist patterns 52 were formed in a circular shape on the matrix 51. The diameter of the circular shape is 32 µm, and the thickness is 1 µm. The center-to-center distance between the respective resist patterns 52 is 40 µm. Further, as a resist, there was used EPPR-A (trade name) manufactured by Tokyo Ohka Kogyo Co., Ltd., a polyimide-based resist, which was used in Example 1. A spin coat method was employed for application of the resist. An EPPR developer manufactured by Tokyo Ohka Kogyo Co., Ltd. was used as a developer. The exposure amount was adjusted to from 50 to 100 mJ/cm2.

Subsequently, as shown in FIG. 5(*c*), platinum was plated on the matrix 51 by thick electroplating, and an electroformed film 53 was deposited. The electroformed film 53 was initially deposited on a portion of the matrix 51 which was not covered with the resist pattern 52, and grew only in a direction perpendicular to a plane of the matrix 51 (in a longitudinal direction). However, when the thickness of the electroformed film 53 reached the thickness of the resist pattern 52 or more, the electroformed film 53 grew also in a direction parallel to the plane of the matrix 51 (in a lateral direction).

Thereafter, the thick electroplating was stopped before the resist pattern 52 was completely covered with the electroformed film 53. Incidentally, the desired diameter of through holes of the nebulizer mesh is 2.5 µm. The cross-sectional shape of a part of the through hole obtained was observed under an electron microscope.

Figure 10:
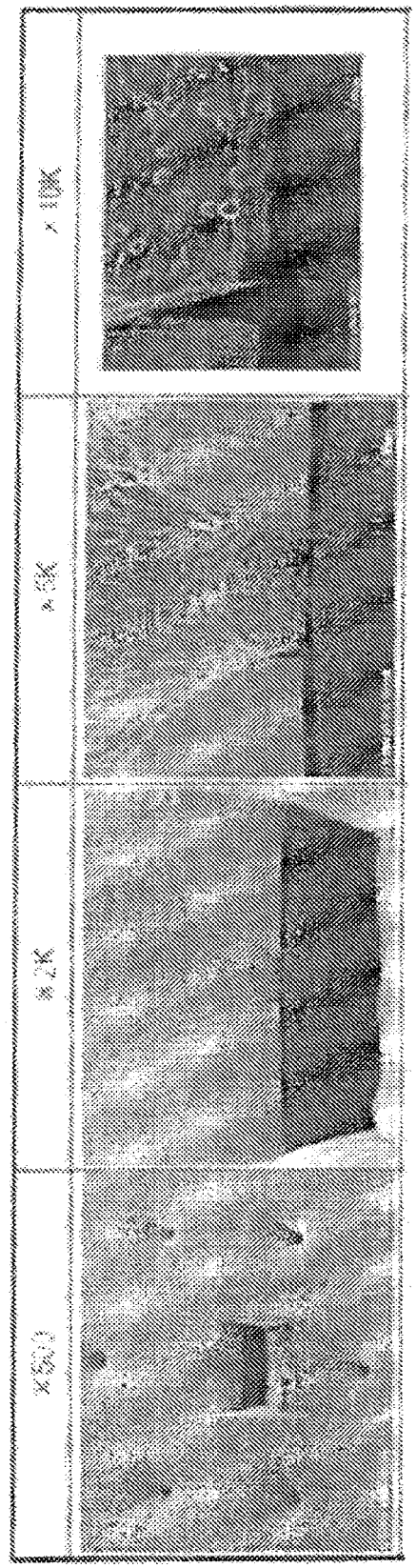
FIGS. 10(a) to 10(d) are cross-sectional photographs of a part of a through hole of a nebulizer mesh obtained in Comparative Example 1.
Figure 11:
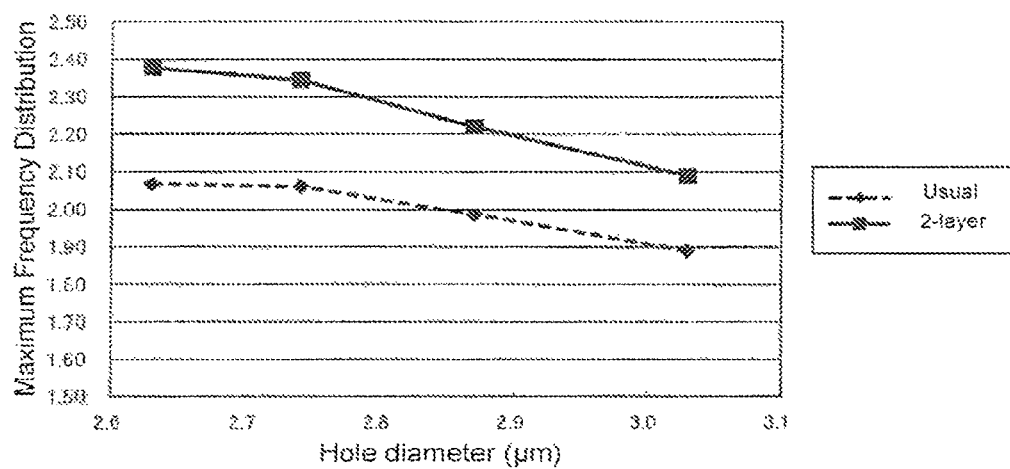
FIG. 11 is a view showing the results of Table 2 graphically for changes in maximum frequency distribution for each hole diameter.
Figure 12:
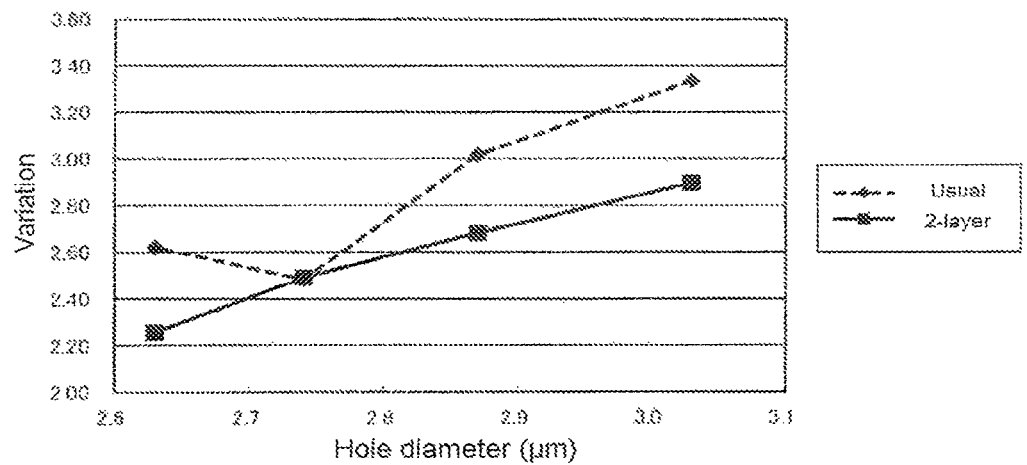
FIG. 12 is a view showing the results of Table 2 graphically for changes in variation for each hole diameter.

FIG. 10 shows cross-sectional photographs of a part of the through hole of the nebulizer mesh obtained in Comparative Example 1. The magnification of FIG. 10 is 500× in 10(*a*), 2000× in 10(*b*), 5000× in 10(*c*), and 10000× in 10(*d*). As shown in FIG. 10, it has been known that the shape of the through hole forms an opening opened in a mortar shape from one surface to the other surface. Incidentally, the cylindrical space portion illustrated in Example 1 described above has not been observed.

Incidentally, the composition of a plating liquid used in Comparative Example 1 was the same as in Example 1. Further, the thickness of the nebulizer mesh was 20 µm.

Example 5

A nebulizer mesh was prepared according to the procedure described in Example 1.

However, a first resist pattern 421 is in a circular shape having a diameter of 32 µm, and has a thickness of 1 µm. A second resist pattern 422 is in a cylindrical shape having a diameter of 2.5 µm and a height of 6 µm. Further, the number of through holes in the nebulizer mesh was set to 10,000.

The nebulizer mesh obtained was installed in a nebulizer equipped with a horn vibrator. A physiological saline solution was supplied as a liquid to a region in which the vibrator and the mesh were in contact with each other, and atomized. The nebulized particle diameter of the nebulized particles was measured by a laser optical diffraction method using a particle diameter measurement apparatus (manufactured by SYMPATEC Corporation, product name: HELOS/BR-Multi), and the mean particle diameter in the case where all measured particles were arranged on the volume basis (VIVID) was calculated. Further, the maximum frequency distribution value and variation were examined from the frequency distribution of the nebulized particle diameter on the volume basis.

The maximum frequency distribution value as used herein means a value (volume %) indicating the highest frequency of the frequency distribution. The variation means a value obtained by subtracting a value of the nebulized particle diameter μm at the time when accumulation reaches 10% from a value of the nebulized particle diameter μm at the time when accumulation from the small nebulized particle diameter reaches 90%, from the frequency distribution measured with the particle diameter measurement apparatus, and dividing this value by 2.

Further, the relationship between the hole diameter value of the nebulizer mesh prepared and each of the VIVID, the maximum frequency distribution of the nebulized particle diameter (the peak value of a frequency distribution graph) and the variation was examined. Incidentally, the nebulizer mesh prepared by the procedure described in Comparative Example 1 as comparison was also used (referred to as usual). However, the resist pattern 52 is in a circular shape having a diameter of 32 μm, and the thickness is 1 μm. Furthermore, the number of through holes in the nebulizer mesh was set to the same as in Example 1.

The hole diameter means the average value of diameters of about 10,000 holes which are opened on the matrix 41 side of the nebulizer mesh, and is obtained by the following method. From a SEM observation image on the matrix 41 side of the nebulizer mesh, 30 holes are randomly selected, and the average value of the diameters of the holes was determined by image measurement.

The results thereof are shown in Table 1. The measurement was performed for 3 lots of the mesh indicating each hole diameter. The usual resist described in Table 1 indicates the conventional type mesh prepared by the method described in Comparative Example 1, and the two-layer resist indicates the mesh of the present invention prepared by the method described in Example 5.

TABLE 1

| | Hole Diameter (μm) | VMD (μm) (Volume Basis Mean Particle Diameter) | Maximum Frequency Distribution Value | Variation |
|---|---|---|---|---|
| Usual Resist | 3.0 | 5.26 | 1.86 | 3.76 |
| | | 4.66 | 2.05 | 2.82 |
| | | 4.99 | 1.76 | 3.43 |
| | 2.6 | 4.41 | 2.11 | 2.48 |
| | | 4.41 | 2.09 | 2.52 |
| | | 4.85 | 2.00 | 2.87 |
| Two-layer Resist | 3.0 | 4.59 | 2.04 | 2.78 |
| | | 4.68 | 2.08 | 2.85 |
| | | 4.79 | 2.15 | 3.07 |
| | 2.6 | 4.41 | 2.34 | 2.48 |
| | | 4.4 | 2.44 | 2.19 |
| | | 4.27 | 2.35 | 2.11 |

As shown in Table 1, for a hole diameter of from 3.02 to 3.05, the VIVID of the usual resist was from 4.66 to 5.26. On the other hand, for the same hole diameter, the VIVID of the two-layer resist was from 4.59 to 4.79. Similarly, for a hole diameter of from 2.62 to 2.64, the VIVID of the usual resist was from 4.41 to 4.85. Further, the VIVID of the two-layer resist was from 4.27 to 4.41.

From these results, it is presumed that the two-layer is more uniform in the nebulized particle diameter than the usual. Further, the two-layer resist shows a small value in within-lot variation of each hole diameter compared to the usual resist, so that it is presumed that the two-layer resist is more uniform in the nebulized particle diameter.

Furthermore, changes in the variation of nebulized particle diameter and changes in the maximum frequency distribution value (the peak value of the frequency distribution graph) in each hole diameter were examined. The results thereof are shown in Table 2 and FIGS. 11 and 12. The usual resist (usual) described in Table 2 indicates the conventional type mesh prepared by the method described in Comparative Example, and the two-layer resist (two-layer) indicates the mesh of the present invention prepared by the method described in Example.

TABLE 2

| Average n = 3 | Hole Diameter (μm) | VMD (μm) (Volume Basis Mean Particle Diameter) | Maximum Frequency Distribution Value (visual observation of graph) | Variation |
|---|---|---|---|---|
| Usual Resist | 3.0 | 4.97 | 1.89 | 3.34 |
| | 2.9 | 4.64 | 1.99 | 3.02 |
| | 2.7 | 4.26 | 2.06 | 2.48 |
| | 2.6 | 4.56 | 2.07 | 2.62 |
| Two-layer Resist | 3.0 | 4.69 | 2.09 | 2.90 |
| | 2.9 | 4.55 | 2.22 | 2.68 |
| | 2.7 | 4.30 | 2.34 | 2.49 |
| | 2.6 | 4.36 | 2.38 | 2.26 |

FIG. 11 shows the maximum frequency distribution value to the hole diameter. As shown in Table 2 and FIG. 11, the two-layer resist is increased in the maximum frequency distribution value by from about 0.2 to about 0.3, compared to the usual resist. That is to say, the peak of the frequency distribution becomes sharp, so that the nebulized particle diameter is considered to be equalized. For this reason, it is suggested that the two-layer resist can perform more stable nebulization.

FIG. 12 shows the variation of the nebulized particle diameter to the hole diameter. As shown in FIG. 12, the two-layer resist has a tendency to decrease the variation, compared to the usual resist. Accordingly, the nebulized particle diameter is considered to be more equalized by the two-layer resist.

While the present invention has been described in detail with reference to the specific embodiments, it is apparent to those skilled in the art that various changes and modifications can be made without departing from the spirit and scope of the present invention. This application is based on Japanese Patent Application No. 2013-011130 filed on Jan. 24, 2013, which is incorporated by reference herein in its entirety.

INDUSTRIAL APPLICABILITY

The nebulizer mesh of the present invention can be used in medical equipment such as an inhalator, a beauty instrument such as a facial care device, and the like.

DESCRIPTION OF REFERENCE NUMERALS AND SIGNS

10: Inhalator
11: Mesh
12: Casing
13: Vibrator
14: Tank
15: Liquid
16: Mesh support
17: Through hole
41: Matrix
421: First resist pattern 422: Second resist pattern
43: Electroformed film
172: Opening
174: Cylindrical space portion

The invention claimed is:

1. A method for producing a nebulizer mesh which is used, in a nebulizer for atomizing and nebulizing liquid, for atomizing the liquid, and has plural through holes, comprising:

a first step of forming a first resist pattern in a predetermined shape on a matrix; a second step of subsequently forming a second resist pattern in a cylindrical shape on the first resist pattern; a third step of performing metal plating and forming through holes of the nebulizer mesh, after the second step; and a fourth step of removing the matrix and the first and second resist patterns, wherein each of the through holes formed by the third step forms a cylindrical space portion on one surface side of the nebulizer mesh and forms an opening opened in a mortar shape on the other surface side, and the shape of the cylindrical space portion of the through hole is determined by the shape of the second resist pattern formed in the second step.

2. The method for producing a nebulizer mesh according to claim 1, wherein the nebulizer mesh is composed of platinum as a main component.

3. The method for producing a nebulizer mesh according to claim 2, wherein the cylindrical space portion has a height of from 0.1 μm to 20 μm.

4. The method for producing a nebulizer mesh according to claim 2, wherein the cylindrical space portion has a diameter of from 0.3 μm to 10 μm.

5. The method for producing a nebulizer mesh according to claim 2, wherein a resist for forming the first resist pattern is a polyimide-based resist, and a resist for forming the second resist pattern is an epoxy-based resist.

6. The method for producing a nebulizer mesh according to claim 1, wherein the cylindrical space portion has a height of from 0.1 μm to 20 μm.

7. The method for producing a nebulizer mesh according to claim 6, wherein the cylindrical space portion has a diameter of from 0.3 μm to 10 μm.

8. The method for producing a nebulizer mesh according to claim 1, wherein the cylindrical space portion has a diameter of from 0.3 μm to 10 μm.

9. The method for producing a nebulizer mesh according to claim 1, wherein a resist for forming the first resist pattern is a polyimide-based resist, and a resist for forming the second resist pattern is an epoxy-based resist.

* * * * *